US010450616B1

(12) United States Patent
Dedent et al.

(10) Patent No.: US 10,450,616 B1
(45) Date of Patent: Oct. 22, 2019

(54) **POLYNUCLEOTIDES FOR THE AMPLIFICATION AND DETECTION OF *CHLAMYDIA TRACHOMATIS***

(71) Applicant: Talis Biomedical Corporation, Menlo Park, CA (US)

(72) Inventors: Andrea Dedent, San Francisco, CA (US); Matt Lee, Santa Clara, CA (US); Shuyuan Ma, San Jose, CA (US); Hédia Maamar, El Dorado Hills, CA (US)

(73) Assignee: Talis Biomedical Corporation, Menlo Park, CA (US)

( * ) Notice: Subject to any disclaimer, the term of this patent is extended or adjusted under 35 U.S.C. 154(b) by 3 days.

(21) Appl. No.: 15/976,733

(22) Filed: May 10, 2018

Related U.S. Application Data

(60) Provisional application No. 62/669,236, filed on May 9, 2018.

(51) Int. Cl.
*C12Q 1/689* (2018.01)
*C12Q 1/682* (2018.01)
*C12Q 1/6844* (2018.01)

(52) U.S. Cl.
CPC ............. *C12Q 1/689* (2013.01); *C12Q 1/682* (2013.01); *C12Q 1/6844* (2013.01); *C12Q 2531/101* (2013.01); *C12Q 2563/107* (2013.01); *C12Q 2600/112* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | |
|---|---|---|
| 9,187,789 B2 | 11/2015 | Pabich et al. |
| 9,434,999 B1 | 9/2016 | Ao et al. |
| 9,982,312 B2 | 5/2018 | Pearce et al. |
| 2013/0265054 A1 | 10/2013 | Lowrery et al. |
| 2015/0322493 A1 | 11/2015 | Tulp et al. |
| 2016/0319378 A1 | 11/2016 | Rey |

FOREIGN PATENT DOCUMENTS

| | | | |
|---|---|---|---|
| CN | 101886122 A | | 11/2010 |
| WO | WO 2011/144304 A1 | | 11/2011 |
| WO | WO 2015/063498 A2 | | 5/2015 |
| WO | WO 2018/089942 | * | 5/2018 |

OTHER PUBLICATIONS

Choopara, I., et al, Rapid and visual Chlamyd a trachomatls detection using loop-mediated Isothennal amplification and hydroxynaphthol blue; Lett Appl MIcrobJol, Sep. 30, 2016, vol. 64, Iss. 1, pp. 51-56.

(Continued)

*Primary Examiner* — Amanda Haney
(74) *Attorney, Agent, or Firm* — Goodwin Procter LLP

(57) ABSTRACT

The invention provides methods and compositions for the detection of *Chlamydia trachomatis* in a test sample. Its presence or absence in the sample is determined by nucleic acid based testing methods using primers and/or probes and or molecular beacons that bind to the 23S ribosomal genes or gene transcripts.

27 Claims, 1 Drawing Sheet

Specification includes a Sequence Listing.

(56) References Cited

OTHER PUBLICATIONS

Jevtusevskaja, J., et al. "Combination with antimicrobial peptide lyses Improves loop-mediated Isothermal amplification based method for Chlamydia trachomatis detection directly in urine sample," BMC Infectious Diseases, Jul. 13, 2016, vol. 16, No. 329, pp. 1-8.

Xu, G., et al. "A capillary-based mulliplexed isothermal nucleic acid-based lest for sexually transmitted diseases in patients," Chem Commun (Camb), Sep. 8, 2016, vol. 52, No. 82, pp. 12187-12190.

PCT International Search Report and Written Opinion for PCT/US2017/061402, dated Apr. 18, 2018, 19 Pages.

Invitation to Pay Additional Fees and, Where Applicable, Protest Fee for PCT/US2017/061402, dated Feb. 12, 2018, 3 pages.

Choopara, I., et al., "Development of Chlamydia trachomatis detection by loop-mediated isothermal amplification," International Journal of Biomedical Science & Bioinformatics, 2015, vol. 2, Issue 1, pp. 21-25.

Little, M., et al. "Strand Displacement Amplification and Homogeneous Real-Time Detection Incorporated in a Second-Generation DNA Probe System, BDProbeTecET." Clinical Chemistry, 1999, vol. 45, No. 6, pp. 777-784.

NG, L.-K., et al., "The laboratory diagnosis of Neisseria gonorrhoeae," Can J Infect Dis Med Microbiol., 2005, vol. 16, No. 1, pp. 15-25.

Njiru, Z., "Loop-Mediated Isothermal Amplification Technology: Towards Point of Care Diagnostics." PLoS Negl Trop Dis., 2015, vol. 6, No. 6, e1572, pp. 1-4.

Nixon, G., et al., "A novel approach for evaluating the performance of real time quantitative loop-mediated isothermal amplification-based methods." Biomolecular Detection and Quantification, 2014, vol. 2, pp. 4-10.

Xu, G., et al., "Rapid ultrasonic isothermal amplification of DNA with multiplexed melting analysis—applications in the clinical diagnosis of sexually transmitted diseases." Chem. Commun., 2015, vol. 51, pp. 2589-2592.

Yamamoto, R., et al., "Molecular beacon aptamer fluoresces in the presence of Tat protein of HIV-1," Genes to Cells, 2000, vol. 5, pp. 389-396.

Zanoli, L., et al., "Isothermal Amplification Methods for the Detection of Nucleic Acids in Microfluidic Devices." Biosensors, 2013, vol. 3, pp. 18-43.

* cited by examiner

| Molecular Beacon | SEQ ID NO | Primer Set | | | | | | | | | | | | | | | |
|---|---|---|---|---|---|---|---|---|---|---|---|---|---|---|---|---|---|
| | | 12, 39, 66 | 13, 40, 67 | 14, 41, 68 | 15, 42, 69 | 16, 43, 70 | 17, 44, 71 | 18, 45, 72 | 19, 46, 73 | 20, 47, 74 | 21, 48, 75 | 22, 49, 76 | 23, 50, 77 | 24, 51, 78 | 25, 52, 79 | 26, 53, 80 | 27, 54, 81 |
| MB1 | 97 | x | x | | | | | | | | | | | | | | |
| MB2 | 98 | x | x | x | x | x | x | x | x | x | x | x | x | x | x | x | x |
| MB3 | 99 | x | x | x | x | x | x | x | x | x | x | x | x | x | x | x | x |
| MB4 | 100 | x | x | x | x | x | x | x | x | x | x | x | x | x | x | x | x |
| MB5 | 101 | x | x | | | | | | | | | | | | | | |
| MB6 | 102 | | x | | | | | | | | | | | | | | |
| MB7 | 103 | x | | x | x | x | x | x | x | x | x | x | x | x | x | x | x |
| MB8 | 104 | x | | x | x | x | x | x | x | x | x | x | x | x | x | x | x |
| MB9 | 105 | x | | x | x | x | x | x | x | x | x | x | x | x | x | x | x |
| MB10 | 106 | x | x | x | x | x | x | x | x | x | x | x | x | x | x | x | x |
| MB11 | 107 | x | | x | x | x | x | x | x | x | x | x | x | x | x | x | x |
| MB12 | 108 | x | | x | x | x | x | x | x | x | x | x | x | x | x | x | x |
| MB13 | 109 | x | | x | x | x | x | x | x | x | x | x | x | x | x | x | x |
| MB14 | 110 | x | x | x | x | x | x | x | x | x | x | x | x | x | x | x | x |
| MB15 | 111 | x | | x | x | x | x | x | x | x | x | x | x | x | x | x | x |
| MB16 | 112 | x | x | x | x | x | x | x | x | x | x | x | x | x | x | x | x |
| MB17 | 113 | | | x | x | x | x | x | x | x | x | x | x | x | x | x | x |
| MB18 | 114 | x | | x | x | x | x | x | x | x | x | x | x | x | x | x | x |
| MB19 | 115 | x | | x | x | x | x | x | x | x | x | x | x | x | x | x | x |
| MB20 | 116 | x | | x | x | x | x | x | x | x | x | x | x | x | x | x | x |
| MB21 | 117 | x | | x | x | x | x | x | x | x | x | x | x | x | x | x | x |
| MB22 | 118 | x | | x | x | x | x | x | x | x | x | x | x | x | x | x | x |
| MB23 | 119 | x | | x | x | x | x | x | x | x | x | x | x | x | x | x | x |
| MB24 | 120 | x | x | x | x | x | x | x | x | x | x | x | x | x | x | x | x |
| MB25 | 121 | x | x | x | x | x | x | x | x | x | x | x | x | x | x | x | x |
| MB26 | 122 | x | x | x | x | x | x | x | x | x | x | x | x | x | x | x | x |
| MB27 | 123 | x | | x | x | x | x | x | x | x | x | x | x | x | x | x | x |
| MB28 | 124 | x | | x | x | x | x | x | x | x | x | x | | | | | x |
| MB29 | 125 | | | x | x | x | x | x | x | x | x | x | | | x | | x |
| MB30 | 126 | x | | x | x | x | x | x | x | x | x | | | x | x | x | x |
| MB31 | 127 | | | x | x | x | x | x | x | x | | x | x | x | x | x | x |
| MB32 | 128 | x | | x | x | x | x | x | x | x | x | x | x | x | x | x | x |
| MB33 | 129 | x | | x | x | x | x | x | x | x | x | x | x | x | x | x | x |
| MB34 | 130 | x | x | x | x | x | x | x | x | x | x | x | x | x | x | x | x |
| MB35 | 131 | x | x | x | x | x | x | x | x | x | x | x | x | x | x | x | x |

POLYNUCLEOTIDES FOR THE AMPLIFICATION AND DETECTION OF *CHLAMYDIA TRACHOMATIS*

CROSS-REFERENCE TO RELATED APPLICATION

This application claims the benefit of U.S. Provisional Application No. 62/669,236, filed May 9, 2018, the disclosure of which incorporated by reference herein in its entirety.

SEQUENCE LISTING

The instant application contains a Sequence Listing which has been submitted via EFS-Web and is hereby incorporated by reference in its entirety. Said ASCII copy, created on Jun. 21, 2018, is named 40570US_CRF_sequencelisting.txt, and is 29,947 bytes in size.

FIELD OF THE INVENTION

The present invention relates to the fields of molecular biology and nucleic acid chemistry. The invention provides methods and reagents for detecting pathogens, such as *Chlamydia trachomatis* and accordingly, also relates to the fields of medical diagnostics and prognostics. In particular, the invention relates to polynucleotides and methods for amplifying and detecting *Chlamydia trachomatis*.

BACKGROUND OF THE INVENTION

There is an urgent need for the development of a rapid, affordable, sample-in answer-out point of care (POC) diagnostic platform for sexually transmitted infections (STIs). The World Health Organization (WHO) estimates that more than 499 million new cases of curable STIs, namely those due to *Neisseria gonorrhoeae* (NG), *Chlamydia trachomatis* (CT), *Trichomonas vaginalis* (TV) and Syphilis occur every year worldwide in men and women aged 15-49 years, causing significant morbidity and mortality. Untreated gonococcal and chlamydial infections in women in sub-Saharan Africa have been implicated as the cause of up to 85% of infertility among women seeking infertility intervention.

*C. trachomatis* is responsible for the most common sexually transmitted infection in the US. *Chlamydia* can cause urethritis in men and pelvic inflammatory disease, ectopic pregnancy and infertility in women. Asymptomatic infections are common both in men and women which warrants screenings to prevent the spread of the disease (as recommended by the CDC).

BRIEF DESCRIPTION OF THE DRAWINGS

FIG. 1 identifies labeled polynucleotide sequences, or molecular beacons, that are capable of binding to amplicon produced from each primer set.

SUMMARY

The present invention encompasses, in some embodiments, a composition comprising a set of polynucleotides selected from the group consisting of Set-1 through Set-81. In some embodiments, the composition further comprises a probe. In some embodiments, the probe comprises a label. In some embodiments, the probe is a labeled polynucleotide. In a preferred implementation, the label is a fluorophore, which preferably is covalently attached to a terminus of the polynucleotide. In a particularly preferred embodiment, the probe or polynucleotide is a molecular beacon comprising a fluorophore, a quencher, and a polynucleotide. In one embodiment, the fluorophore is FAM and the quencher is BHQ1. In an alternate implementation, the fluorophore is ATTO 565 or Alexa 594 and the quencher is BHQ1 or BHQ2.

In some implementations, composition comprises a labeled polynucleotide comprising a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 6-30 of SEQ ID NO: 102, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, and nucleotides 5-30 of SEQ ID NO: 117, nucleotides 8-28 of SEQ ID NO: 118, nucleotides 8-30 of SEQ ID NO: 119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, nucleotides 6-27 of SEQ ID NO: 130, and nucleotides 8-29 of SEQ ID NO: 131. In further implementations, the labeled polynucleotide can comprise a sequence selected from the group consisting of SEQ ID NOs: 97 through 131. In certain implementations, the sequence of the labeled polynucleotide is selected from the group consisting of SEQ ID NOs: 97 through 131. In other embodiments, the sequence of the labeled polynucleotide is selected from the group consisting of SEQ ID NOs: 97 through 131.

In some embodiments, the set of polynucleotides is selected from the group consisting of Set-12, Sets 14-27, Set-29, Sets 41-54, Set-66, and Sets 68-81, and the composition comprises a labeled polynucleotide comprising a sequence selected from the group consisting of nucleotides 5-26 of SEQ ID NO: 103, nucleotides 4-27 of SEQ ID NO: 104, nucleotides 7-30 of SEQ ID NO: 105, nucleotides 6-29 of SEQ ID NO: 107, nucleotides 6-29 of SEQ ID NO: 108, nucleotides 6-29 of SEQ ID NO: 109, nucleotides 8-31 of SEQ ID NO: 111, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, nucleotides 9-34 of SEQ ID NO: 123, nucleotides 8-34 of SEQ ID NO: 124, nucleotides 7-32 of SEQ ID NO: 128, and nucleotides 4-27 of SEQ ID NO: 129. In some implementations, the labeled polynucleotide comprises a sequence selected from the group consisting of SEQ ID NO: 103, SEQ ID NO: 104, SEQ ID NO: 105, SEQ ID NO: 107, SEQ ID NO: 108, SEQ ID NO: 109, SEQ ID NO: 111, SEQ ID NO: 114, SEQ ID NO: 115, SEQ ID NO: 116, SEQ ID NO: 117, SEQ ID NO: 118, SEQ ID NO: 119, SEQ ID NO: 123, SEQ ID NO: 124, SEQ ID NO: 128, and SEQ ID NO: 129. In some implementations, the sequence of the labeled polynucleotide is SEQ ID NO: 103, SEQ ID NO: 104, SEQ ID NO: 105, SEQ ID NO: 107, SEQ ID NO: 108, SEQ ID NO: 109, SEQ ID NO: 111, SEQ ID NO: 114, SEQ ID NO: 115, SEQ ID NO: 116, SEQ ID NO: 117, SEQ ID NO: 118, SEQ ID NO: 119, SEQ ID NO: 123, SEQ ID NO: 124, SEQ ID NO: 128, and SEQ ID NO: 129. In a preferred implementation, the sequence of the labeled polynucleotide is SEQ ID NO: 115, and the set of polynucleotides is selected from the group consisting of Set-20, Set-24, Set-47, Set-51, Set-74 and Set-78. Even more preferably, the set of polynucleotides is Set-20 or Set-24.

In yet another embodiment, the set of polynucleotides is selected from the group consisting of Sets 12-27, Sets 39-54, and Sets 66-81, and the composition comprises a labeled polynucleotide comprising a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 5-27 of SEQ ID NO: 106, nucleotides 6-30 of SEQ ID NO: 110, nucleotides 6-29 of SEQ ID NO: 112, nucleotides 8-29 of SEQ ID NO: 120, nucleotides 4-33 of SEQ ID NO: 121, and nucleotides 7-34 of SEQ ID NO: 122. More particularly, the labeled polynucleotide can comprise a sequence selected from the group consisting of SEQ ID NO: 97, SEQ ID NO: 98, SEQ ID NO: 99, SEQ ID NO: 100, SEQ ID NO: 101, SEQ ID NO: 106, SEQ ID NO: 110, SEQ ID NO: 112, SEQ ID NO: 120, SEQ ID NO: 121, and SEQ ID NO: 122. In certain implementations, the sequence of the labeled polynucleotide is selected from the group consisting of SEQ ID NO: 97, SEQ ID NO: 98, SEQ ID NO: 99, SEQ ID NO: 100, SEQ ID NO: 101, SEQ ID NO: 106, SEQ ID NO: 110, SEQ ID NO: 112, SEQ ID NO: 120, SEQ ID NO: 121, and SEQ ID NO: 122.

In one implementation, the set of polynucleotides is selected from the group consisting of Set-12, Sets 14-18, Set-20, Set-24, Set-27, Set-39, Sets 41-45, Set-47, Set-51, Set-54, Set-66, Sets 68-72, Set 74, Set-78, and Set-81, and the composition comprises a labeled polynucleotide comprising a sequence selected from the group consisting of nucleotides 6-28 of SEQ ID NO: 125 and nucleotides 7-28 of SEQ ID NO: 126. In certain implementations, the labeled polynucleotide comprises a sequence selected from the group consisting of SEQ ID NO: 125 and SEQ ID NO: 126. In some embodiments, the sequence of the labeled polynucleotide is SEQ ID NO: 125 or SEQ ID NO: 126.

In another implementation, the set of polynucleotides is selected from the group consisting of Sets 14-27, Sets 41-54, and Sets 68-81, and the composition comprises a labeled polynucleotide comprising a sequence selected from the group consisting of nucleotides 8-31 of SEQ ID NO: 113 and nucleotides 3-27 of SEQ ID NO: 127. In some embodiments, the labeled polynucleotide comprises a sequence selected from the group consisting of SEQ ID NO: 113 and SEQ ID NO: 127. In other embodiments, the sequence of the labeled polynucleotide is SEQ ID NO: 113 or SEQ ID NO: 127.

In yet another embodiment, the set of polynucleotides is selected from the group consisting of Sets 12-20, Sets 22-27, Sets 39-47, Sets 49-54, Sets 66-74, and Sets 76-81, and the composition comprises a labeled polynucleotide comprising nucleotides 6-27 of SEQ ID NO: 130. In some implementations, the labeled polynucleotide comprises SEQ ID NO: 130. In other embodiments, the sequence of the labeled polynucleotide is SEQ ID NO: 130.

In one implementation, the set of polynucleotides is selected from the group consisting of Set-13, Set-40 and Set-67, and the composition comprises a labeled polynucleotide comprising a sequence selected from the group consisting of nucleotides 6-30 of SEQ ID NO: 102 and nucleotides 8-29 of SEQ ID NO: 131. In such an embodiment, the labeled polynucleotide can comprise a sequence selected from the group consisting of SEQ ID NO: 102 and SEQ ID NO: 131. In another embodiment, the sequence of the labeled polynucleotide is SEQ ID NO: 102 or SEQ ID NO: 131.

Another aspect of the invention provides molecular beacons comprising a fluorophore, a quencher, and a polynucleotide, wherein the polynucleotide comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 6-30 of SEQ ID NO: 102, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, and nucleotides 8-29 of SEQ ID NO: 120.

Yet another aspect of the invention provides methods of detecting *Chlamydia trachomatis* in a test sample, the method comprising (a) extracting nucleic acid from the test sample, (b) amplifying a target sequence by reacting the nucleic acid extracted in step (a) with a reaction mixture comprising a strand displacement DNA polymerase and a sequence-specific primer set, wherein said sequence-specific primer set is selected from the group consisting of Set-1 through Set-81, and (c) detecting the presence or absence of an amplified product of step (b); wherein the presence of said amplification product is indicative of the presence of *Chlamydia trachomatis* in the test sample. In one embodiment, the amplification in step (b) of the target sequence is performed at between about 60° C. and about 67° C. for less than 30 minutes. Preferably, the amplification step is performed for less than fifteen minutes, less than ten minutes or less than six minutes. In some implementations, the reaction mixture further comprises a reverse transcriptase. In some implementations, *Chlamydia trachomatis* is present in the test sample at a concentration of ≤100 IFU/mL, ≤50 IFU/mL, ≤5 IFU/mL, or even ≤2 IFU/mL. In one implementation, *Chlamydia trachomatis* is present in the test sample at a concentration of ≤5 IFU/ml and the amplification step is performed for less than 15 minutes. In another implementation, *Chlamydia trachomatis* is present in the test sample at a concentration of ≤10 IFU/ml and the amplification step is performed for less than six minutes.

In certain embodiments, detecting the presence or absence of the amplification product comprises hybridizing the amplified product with a probe comprising a polynucleotide attached to a label. In a preferred implementation, the label is a fluorophore, which preferably is covalently attached to a terminus of the polynucleotide. In a particularly preferred embodiment, the probe or polynucleotide is a molecular beacon comprising a fluorophore, a quencher, and a polynucleotide. In one embodiment, the fluorophore is FAM and the quencher is BHQ1. In an alternate implementation, the fluorophore is ATTO 565 or Alexa 594 and the quencher is BHQ1 or BHQ2. This method can be practiced using any combination of primer set and labeled polynucleotide, e.g. molecular beacon, described herein. FIG. 1 identifies labeled polynucleotide sequences, or molecular beacons, that are capable of binding to the amplicon resulting from each primer set, and therefore are useful in detecting the presence of *Chlamydia trachomatis* in a test sample.

Yet another aspect of the invention provides kits comprising the compositions comprising a set of polynucleotides selected from the group consisting of Set-1 through Set-81. In some embodiments, the kit further comprises a strand displacement polymerase and, optionally, a reverse transcriptase. In certain embodiments, the kit comprises a molecular beacon comprising a fluorophore, a quencher, and a polynucleotide, wherein the polynucleotide comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 6-30 of SEQ ID NO: 102, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, nucleotides 6-27 of SEQ ID NO: 130, and nucleotides 8-29 of SEQ ID NO: 131. The polynucleotide sequence of the molecular beacon can comprise a sequence selected from the group consisting of SEQ ID NO: 97 through SEQ ID NO: 131. In some embodiments, the polynucleotide sequence of the molecular beacon consists of a sequence selected from the group consisting of SEQ ID NO: 97 through SEQ ID NO: 131. In one embodiment, the polynucleotide sequence of the molecular beacon consists of SEQ ID NO: 115 and the set of polynucleotides is Set-20 or Set-24.

Yet another aspect of the invention provides methods of detecting *Chlamydia trachomatis* in a test sample, the method comprising (a) extracting nucleic acid from the test sample, (b) amplifying a target sequence by reacting the nucleic acid extracted in step (a) for less than ten minutes with a reaction mixture comprising a strand displacement DNA polymerase and a sequence-specific LAMP primer set, and (c) detecting the presence or absence of an amplified product of step (b); wherein the presence of said amplification product is indicative of the presence of *Chlamydia trachomatis* in the test sample. In some implementations, *Chlamydia trachomatis* is present in the test sample at a concentration of ≤100 IFU/mL, ≤50 IFU/mL, ≤5 IFU/mL, or even ≤2 IFU/mL. In certain implementations, the amplifying step comprises reacting the nucleic acid extracted in step (a) with a reaction mixture comprising a strand displacement DNA polymerase and a sequence-specific primer set, wherein said sequence-specific primer set is selected from the group consisting of Set-1 through Set-81. In such implementations, detecting the presence or absence of the amplification product can comprise hybridizing the amplified product with a molecular beacon comprising a polynucleotide sequence selected from the group consisting of SEQ ID NO: 97 through SEQ ID NO: 131. In some implementations, detecting the presence or absence of the amplification product comprises hybridizing the amplified product with a molecular beacon comprising a polynucleotide sequence selected from the group consisting of SEQ ID NO: 99 through SEQ ID NO: 120.

In some embodiments of the methods described herein, the test sample comprises one or more other microorganisms in addition to *Chlamydia trachomatis*, and wherein the target sequence from *Chlamydia trachomatis* is preferentially amplified over a polynucleotide sequence from the one or more other microorganisms.

In some embodiments, the invention provides a nucleic acid sequence at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to any one of SEQ ID NOs 1-96 and methods of using those nucleic acid sequences to detect *Chlamydia trachomatis* in a test sample. In some embodiments, the invention provides a nucleic acid sequence at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to any one of the group consisting of nucleotides 3-31 of SEQ ID NO: 99, nucleotides 5-30 of SEQ ID NO: 100, nucleotides 6-29 of SEQ ID NO: 101, nucleotides 6-30 of SEQ ID NO: 102, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, and nucleotides 5-30 of SEQ ID NO: 117 and methods of using those nucleic acid sequences to detect *Chlamydia trachomatis* in a test sample.

DETAILED DESCRIPTION

Detecting low concentrations of species (down to a few molecules or microorganisms in a sample) is a challenge in medicine. The present invention relates to the selective detection of *Chlamydia trachomatis*. In particular, based on new detection strategies utilizing nucleic acid amplification, particularly RT-LAMP, and molecular beacon detection, *Chlamydia* infections can be diagnosed using the methods and reagents described herein. Using RNA (either ribosomal RNA (rRNA) or messenger RNA) as the target regions provides multiple copies of the target per *C. trachomatis* genome. Accordingly, this facilitates the detection of *C. trachomatis* in samples utilizing the approaches described herein relative to techniques that target genomic DNA, even when present in multiple copies per genome. In addition, the molecular beacon detection reagents described herein provide additional specificity, failing to bind, in most cases, to off target amplified DNA, thereby minimizing the occurrence of, e.g., false positives. This specificity is illustrated in, inter alia, Example 4 provided below. Many other features of the invention are also described herein.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. The term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose).

As used herein, a "polynucleotide" refers to a polymeric chain containing two or more nucleotides, which contain deoxyribonucleotides, ribonucleotides, and/or their analog, such as those containing modified backbones (e.g. peptide nucleic acids (PNAs) or phosphorothioates) or modified bases. "Polynucleotides" includes primers, oligonucleotides, nucleic acid strands, etc. A polynucleotide may contain standard or non-standard nucleotides. Thus, the term includes mRNA, tRNA, rRNA, ribozymes, DNA, cDNA, recombinant nucleic acids, branched nucleic acids, plasmids, vectors, probes, primers, etc. Typically, a polynucleotide contains a 5' phosphate at one terminus ("5' terminus") and a 3' hydroxyl group at the other terminus ("3' terminus") of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide. Where nucleic acid of the invention takes the form of RNA, it may or may not have a 5' cap.

LAMP is a nucleic acid amplification method that relies on auto-cycle strand-displacement DNA synthesis performed by a Bst DNA polymerase, or other strand displacement polymerases. The amplified products are stem-loop structures with several repeated sequences of the target, and have multiple loops. The principal merit of this method is that denaturation of the DNA template is not required, and thus the LAMP reaction can be conducted under isothermal conditions (ranging from 60 to 67° C.). LAMP requires only one enzyme and four types of primers that recognize six distinct hybridization sites in the target sequence. The reaction can be accelerated by the addition of two additional primers. The method produces a large amount of amplified product, resulting in easier detection, such as detection by visual judgment of the turbidity or fluorescence of the reaction mixture.

In brief, the reaction is initiated by annealing and extension of a pair of 'loop-forming' primers (forward and backward inner primers, FIP and BIP, respectively), followed by annealing and extension of a pair of flanking primers (F3 and B3). Extension of these primers results in strand-displacement of the loop-forming elements, which fold up to form terminal hairpin-loop structures. Once these key structures have appeared, the amplification process becomes self-sustaining, and proceeds at constant temperature in a continuous and exponential manner (rather than a cyclic manner, like PCR) until all of the nucleotides (dATP, dTTP, dCTP & dGTP) in the reaction mixture have been incorporated into the amplified DNA. Optionally, an additional pair of primers can be included to accelerate the reaction. These primers, termed Loop primers, hybridize to non-inner primer bound terminal loops of the inner primer dumbbell shaped products.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

LAMP allows amplification of target DNA sequences with higher sensitivity and specificity than PCR, often with reaction times of below 30 minutes, which is equivalent to the fastest real-time PCR tests. The target sequence which is amplified is typically 200-300 base-pairs (bp) in length, and the reaction relies upon recognition of between 120 bp and 160 bp of this sequence by several primers simultaneously during the amplification process. This high level of stringency makes the amplification highly specific, such that the appearance of amplified DNA in a reaction occurs only if the entire target sequence was initially present.

Applications for LAMP have been further extended to include detection of RNA molecules by addition of Reverse Transcriptase enzyme (RT). By including RNA detection, the types of targets for which LAMP can be applied are also expanded and add the ability to additionally target RNA based viruses, important regulatory non-coding RNA (sRNA, miRNA), and RNA molecules that have been associated with particular disease or physiological states. The ability to detect RNA also has the potential to increase assay sensitivity, for instance in choosing highly expressed, stable, and/or abundant messenger RNA (mRNA) or ribosomal RNA (rRNA) targets. This preliminary phase of amplification involves the reverse transcription of RNA molecules to complementary DNA (cDNA). The cDNA then serves as template for the strand displacing DNA polymerase. Use of a thermostable RT enzyme (i.e., NEB RTx) enables the reaction to be completed at a single temperature and in a one step, single mix reaction.

A "target sequence," as used herein, means a nucleic acid sequence of *Chlamydia trachomatis*, or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence can also be single stranded, e.g., RNA. A target sequence may be selected that is more or less specific for a particular organism. For example, the target sequence may be specific to an entire genus, to more than one genus, to a species or subspecies, serogroup, auxotype, serotype, strain, isolate or other subset of organisms.

The speed, specificity and sensitivity of the primers/probe compositions and method described herein result from several aspects. Exemplary primers for use in the compositions and methods according to the present invention include:

TABLE 1

Primer Sequences

| Sequence ID | Sequence (5' to 3') |
| --- | --- |
| SEQ ID NO: 1 | CGAAGGAATGACGGAGTA |
| SEQ ID NO: 2 | CGCCTTAGAATATTCATCTCG |
| SEQ ID NO: 3 | GCGACCTGATCTTATGTTAGCGCGATTGGAAGAGTCCGTA |
| SEQ ID NO: 4 | GAACCGATGGTGTGGAGCCCACCTGTGTCGGTT |
| SEQ ID NO: 5 | CTACTAACCGTTCTCATCGC |
| SEQ ID NO: 6 | CTGTTGATGGTGACCGTAC |
| SEQ ID NO: 7 | AAAACTATAGCGAAGGAATGACGGA |
| SEQ ID NO: 8 | TAATTTGCCGAGTTCCTTAACGAAAG |

TABLE 1-continued

Primer Sequences

| Sequence ID | Sequence (5' to 3') |
|---|---|
| SEQ ID NO: 9 | CCCCGAAGATTCCCCTTGATCGCCGTAGAGCGATGAGAACGGTT |
| SEQ ID NO: 10 | GGTGTGGAGCGAGGCTTTCAAGAAATAATATTCATCTCGCCCACCTGTG |
| SEQ ID NO: 11 | TGATCTTATGTTAGCGGATTTGCCTACT |
| SEQ ID NO: 12 | TTTCTAGCTGTTGATGGTGACCGT |
| SEQ ID NO: 13 | AACTATAGCGAAGGAATGACGGAG |
| SEQ ID NO: 14 | TAATTTGCCGAGTTCCTTAACGAAAG |
| SEQ ID NO: 15 | CCCCGAAGATTCCCCTTGATCGCCGTAGAGCGATGAGAACGGTT |
| SEQ ID NO: 16 | GGTGTGGAGCGAGGCTTTCAAGAAATAATATTCATCTCGCCCACCTGTG |
| SEQ ID NO: 17 | TGATCTTATGTTAGCGGATTTGCCTACT |
| SEQ ID NO: 18 | GTTGATGGTGACCGTACCAAAACC |
| SEQ ID NO: 19 | ATAGCGAAGGAATGACGGAGTAAG |
| SEQ ID NO: 20 | TAATTTGCCGAGTTCCTTAACGAAAG |
| SEQ ID NO: 21 | CCCCGAAGATTCCCCTTGATCGCCGTAGAGCGATGAGAACGGTT |
| SEQ ID NO: 22 | GGTGTGGAGCGAGGCTTTCAAGAAATAATATTCATCTCGCCCACCTGTG |
| SEQ ID NO: 23 | GACCTGATCTTATGTTAGCGGATTTGC |
| SEQ ID NO: 24 | TTTCTAGCTGTTGATGGTGACCGT |
| SEQ ID NO: 25 | AGAAGCGAGTCCGGGAGAT |
| SEQ ID NO: 26 | CTGCTGAATACTACGCTCTCCTAC |
| SEQ ID NO: 27 | CCAACATTCCAACTGTCTTCGAATCATCACTCAGCCCAGACCGCCG |
| SEQ ID NO: 28 | GCGTAACAGCTCACCAATCGAGAATCATTGTCTTATCGACACACCCGC |
| SEQ ID NO: 29 | TTACCCACTTAGCATAAAATTAGGGACCTTAA |
| SEQ ID NO: 30 | ACGGGACTAAGCATAAAACCGACA |
| SEQ ID NO: 31 | AGAAGCGAGTCCGGGAGAT |
| SEQ ID NO: 32 | CCGGTACACCTTCTCTGCTG |
| SEQ ID NO: 33 | AAGCCAACATTCCAACTGTCTTCGAATCATCAGCCCAGACCGCCG |
| SEQ ID NO: 34 | GCGTAACAGCTCACCAATCGAGAATCATTGTCTTATCGACACACCCGC |
| SEQ ID NO: 35 | TTACCCACTTAGCATAAAATTAGGGACCTTAA |
| SEQ ID NO: 36 | ACGGGACTAAGCATAAAACCGACA |
| SEQ ID NO: 37 | CACAGGTGGGCGAGATGAATAT |
| SEQ ID NO: 38 | CTGACATATCCCTTTAACCTTTTGGC |
| SEQ ID NO: 39 | ATAGTCACCCTAAAAGGCTCCCCTTATTCCAGGCGCGCGAGATAACTTT |
| SEQ ID NO: 40 | AGAAATGGCCCAGGCGACTGTTTAGGCAGGCGTCACACCATATACT |
| SEQ ID NO: 41 | GGGATAATTTGCCGAGTTCCTTAACG |
| SEQ ID NO: 42 | AAAACACAGCACTATGCAAACCTCTAAG |
| SEQ ID NO: 43 | CACAGGTGGGCGAGATGAAT |
| SEQ ID NO: 44 | CTGACATATCCCTTTAACCTTTTGGC |
| SEQ ID NO: 45 | ATAGTCACCCTAAAAGGCTCCCCTTATTCCAGGCGCGCGAGATAACTTT |
| SEQ ID NO: 46 | AGAAATGGCCCAGGCGACTGTTTAGGCAGGCGTCACACCATATACT |
| SEQ ID NO: 47 | GGGATAATTTGCCGAGTTCCTTAACG |
| SEQ ID NO: 48 | AAAACACAGCACTATGCAAACCTCTAAG |
| SEQ ID NO: 49 | ATTCGAAGACAGTTGGAATGT |
| SEQ ID NO: 50 | TATTATCGGCGCAATGATTCTCGAGGCTTAGAGGCAGCAATC |
| SEQ ID NO: 51 | GTGAGCTGTTACGCACTCT |
| SEQ ID NO: 52 | TCGTTACTTATGCCATGGATC |
| SEQ ID NO: 53 | TAAACGGGACTAAGCATAAAACCGACCTTCTCTGCTGAATACTACG |
| SEQ ID NO: 54 | GATAAGACACGCGGTAGGAG |
| SEQ ID NO: 55 | CTTACCAACGAAATCAAACTC |
| SEQ ID NO: 56 | CACTTAGCATAAAATTAGGGACCTTAATCGGGGGCTAAGCTTCGT |
| SEQ ID NO: 57 | GCGGTCTGGGCTGTTC |
| SEQ ID NO: 58 | TATCGGCGCAATGATTCTC |
| SEQ ID NO: 59 | TGGGTAAGGAAGTGATGATTCGAAGGGTGAGCTGTTACGCAC |
| SEQ ID NO: 60 | TGGCTTAGAGGCAGCAATC |
| SEQ ID NO: 61 | ATCGGCGCAATGATTCTCGATGGCTTAGAGGCAGCAATC |
| SEQ ID NO: 62 | CGTTACTTATGCCATGGATCT |
| SEQ ID NO: 63 | TAAGACACGCGGTAGGAGA |
| SEQ ID NO: 64 | GAAATCGAAGAGATTCCCTGTG |
| SEQ ID NO: 65 | GGTGTTGAGGTCGGTCTT |
| SEQ ID NO: 66 | TTATCCTCAATCCTACAACCCCGAGTAGCGGCGAGCGAAAG |
| SEQ ID NO: 67 | GGATCAGGACTCCTAGTTGAACACACTCCTTTCGTCTACGGGAC |
| SEQ ID NO: 68 | CCTTATCAGCTCGGTTTAGGC |
| SEQ ID NO: 69 | GGAAAGATGGATGATACAGGGTG |
| SEQ ID NO: 70 | GTTGTAGGATTGAGGATAAAGGATC |
| SEQ ID NO: 71 | TACTGGTTCACTATCGGTCATT |
| SEQ ID NO: 72 | TCGGTCTTTCTCTCCTTTCGTCTACTCCTAGTTGAACACATCTGGAA |

TABLE 1 -continued

Primer Sequences

| Sequence ID | Sequence (5' to 3') |
|---|---|
| SEQ ID NO: 73 | CCTCAACACCTGAGTAGGACTAGACGCCTTGGAGAGTGGTCTC |
| SEQ ID NO: 74 | GGACTATCACCCTGTATCATCCA |
| SEQ ID NO: 75 | CGTGAAACCTAGTCTGAATCTGG |
| SEQ ID NO: 76 | TATTCCCCTTTCGCTCGC |
| SEQ ID NO: 77 | GGCTATTCCCCTTTCGCTC |
| SEQ ID NO: 78 | TTAGGCTATTCCCCTTTCGC |
| SEQ ID NO: 79 | GCTATTCCCCTTTCGCTCGC |
| SEQ ID NO: 80 | GTTTAGGCTATTCCCCTTTC |
| SEQ ID NO: 81 | CTGAAACATCTTAGTAAGCAGAGG |
| SEQ ID NO: 82 | GTGTCTAGTCCTACTCAGGTG |
| SEQ ID NO: 83 | CCTACAACCCCGAGCCTTATCAAGAGATTCCCTGTGTAGCG |
| SEQ ID NO: 84 | GGACTCCTAGTTGAACACATCTGGATTCTCTCCTTTCGTCTACGG |
| SEQ ID NO: 85 | GCTCGGTTTAGGCTATTCCC |
| SEQ ID NO: 86 | AAGATGGATGATACAGGGTGATAGT |
| SEQ ID NO: 87 | CGAACTGAAACATCTTAGTAAGCAG |
| SEQ ID NO: 88 | CTCCTTTCGTCTACGGGACTA |
| SEQ ID NO: 89 | ATCAGCTCGGTTTAGGCTATTCCCGAAAAGAAATCGAAGAGATTCCCTG |
| SEQ ID NO: 90 | GCTCGGGGTTGTAGGATTGAGGATACCTGTATCATCCATCTTTCCAGAT |
| SEQ ID NO: 91 | CTTTCGCTCGCCGCTAC |
| SEQ ID NO: 92 | GGATCAGGACTCCTAGTTGAACAC |
| SEQ ID NO: 93 | CCTACAACCCCGAGCCTTATCAGAAAAGAAATCGAAGAGATTCCCTG |
| SEQ ID NO: 94 | ATCAGCTCGGTTTAGGCTATTCCCAGAGATTCCCTGTGTAGCG |
| SEQ ID NO: 95 | GCTCGGGGTTGTAGGATTGAGGATATTCTCTCCTTTCGTCTACGG |
| SEQ ID NO: 96 | GCTCGGGGTTGTAGGATTGAGGATACTGTATCATCCATCTTTCCAGATGT |

Detection of the LAMP amplified products can be achieved via a variety of methods. In a preferred embodiment, detection of product is conducted by adding a fluorescently-labeled probe to the primer mix. The term used herein "probe" refers to a single-stranded nucleic acid molecule comprising a portion or portions that are complementary, or substantially complementary, to a target sequence. In certain implementations, the fluorescently-labeled probe is a molecular beacon.

As used herein, "molecular beacon" refers to a single stranded hairpin-shaped oligonucleotide probe designed to report the presence of specific nucleic acids in a solution. A molecular beacon consists of four components; a stem, hairpin loop, end labelled fluorophore and opposite end-labelled quencher (Tyagi et al., (1998) Nature Biotechnology 16:49-53). When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. "Wavelength-shifting Molecular Beacons" incorporate an additional harvester fluorophore enabling the fluorophore to emit more strongly. Current reviews of molecular beacons include Wang et al., 2009, *Angew Chem Int Ed Engl*, 48(5):856-870; Cissell et al., 2009, *Anal Bioanal Chem* 393(1):125-35; Li et al., 2008, *Biochem Biophys Res Comm* 373(4):457-61; and Cady, 2009, *Methods Mol Biol* 554:367-79.

In one implementation, the molecular beacon comprises a fluorophore, a quencher, and a polynucleotide, wherein the polynucleotide comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 6-30 of SEQ ID NO: 102, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, and nucleotides 8-29 of SEQ ID NO: 120. In one embodiment, the polynucleotide comprises a sequence selected from the group consisting of SEQ ID NO: 99 through SEQ ID NO: 120. In another embodiment, the polynucleotide consists of a sequence selected from the group consisting of SEQ ID NO: 99 through SEQ ID NO: 120.

The molecular beacon is preferably used in a composition also comprising a set of sequence-specific LAMP primers. In one implementation, the molecular beacon comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 6-30 of SEQ ID NO: 102, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, and nucleotides 6-27 of SEQ ID NO: 130. In such an implementation, the molecular beacon can comprise a sequence selected from the group consisting of SEQ ID NO: 97 through SEQ ID NO: 130. More preferably, polynucleotide sequence of the molecular beacon consists of a sequence selected from the group consisting of SEQ ID NO: 97 through SEQ ID NO: 130. In a particularly preferred implementation, the polynucleotide sequence of the molecular beacon is SEQ ID NO: 115.

When included in a composition comprising a set of polynucleotides selected from the group consisting of Sets 12-27, Sets 39-54, and Sets 66-81, the molecular beacon preferably comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 5-27 of SEQ ID NO: 106, nucleotides 6-30 of SEQ ID NO: 110, nucleotides 6-29 of SEQ ID NO: 112, nucleotides 8-29 of SEQ ID NO: 120, nucleotides 4-33 of SEQ ID NO: 121, and nucleotides 7-34 of SEQ ID NO: 122. More particularly, the molecular beacon can comprise a sequence selected from the group consisting of SEQ ID NO: 97, SEQ ID NO: 98, SEQ ID NO: 99, SEQ ID NO: 100, SEQ ID NO: 101, SEQ ID NO: 106, SEQ ID NO: 110, SEQ ID NO: 112, SEQ ID NO: 120, SEQ ID NO: 121, and SEQ ID NO: 122. In certain implementations, the polynucleotide sequence of the molecular beacon is selected from the group consisting of SEQ ID NO: 97, SEQ ID NO: 98, SEQ ID NO: 99, SEQ ID NO: 100, SEQ ID NO: 101, SEQ ID NO: 106, SEQ ID NO: 110, SEQ ID NO: 112, SEQ ID NO: 120, SEQ ID NO: 121, and SEQ ID NO: 122.

When included in a composition comprising a set of polynucleotides selected from the group consisting of Set-12, Sets 14-18, Set-20, Set-24, Set-27, Set-39, Sets 41-45, Set-47, Set-51, Set-54, Set-66, Sets 68-72, Set 74, Set-78, and Set-81, the molecular beacon preferably comprises a sequence selected from the group consisting of nucleotides 6-28 of SEQ ID NO: 125 and nucleotides 7-28 of SEQ ID NO: 126. In certain implementations, the molecular beacon can comprise a polynucleotide sequence selected from the group consisting of SEQ ID NO: 125 and SEQ ID NO: 126. In some embodiments, the polynucleotide sequence of the molecular beacon is SEQ ID NO: 125 or SEQ ID NO: 126.

When used in combination with a set of polynucleotides selected from the group consisting of Sets 14-27, Sets 41-54, and Sets 68-81, the molecular beacon preferably comprises a polynucleotide sequence selected from the group consisting of nucleotides 8-31 of SEQ ID NO: 113 and nucleotides 3-27 of SEQ ID NO: 127. In some embodiments, the labeled polynucleotide of the molecular beacon comprises a sequence selected from the group consisting of SEQ ID NO: 113 and SEQ ID NO: 127. In other embodiments, the polynucleotide sequence of the molecular beacon is SEQ ID NO: 113 or SEQ ID NO: 127.

When included in a composition comprising a set of polynucleotides selected from the group consisting of Sets 12-20, Sets 22-27, Sets 39-47, Sets 49-54, Sets 66-74, and Sets 76-81, the molecular beacon preferably comprises nucleotides 6-27 of SEQ ID NO: 130. In some implementations, the molecular beacon comprises SEQ ID NO: 130. In other embodiments, the polynucleotide sequence of the molecular beacon is SEQ ID NO: 130.

When used in combination with a set of polynucleotides selected from the group consisting of Set-13, Set-40 and Set-67, the molecular beacon preferably comprises a sequence selected from the group consisting of nucleotides 6-30 of SEQ ID NO: 102 and nucleotides 8-29 of SEQ ID NO: 131. In such an embodiment, the molecular beacon can comprise a sequence selected from the group consisting of SEQ ID NO: 102 and SEQ ID NO: 131. In another embodiment, the polynucleotide sequence of the molecular beacon is SEQ ID NO: 102 or SEQ ID NO: 131.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The molecular beacon can be composed of nucleic acid only such as DNA or RNA, or it can be composed of a peptide nucleic acid (PNA) conjugate. The fluorophore can be any fluorescent organic dye or a single quantum dot. The quenching moiety desirably quenches the luminescence of the fluorophore. Any suitable quenching moiety that quenches the luminescence of the fluorophore can be used. A fluorophore can be any fluorescent marker/dye known in the art. Examples of suitable fluorescent markers include, but are not limited to, Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow, Texas Red, and the family of ATTO dyes. A quencher can be any quencher known in the art. Examples of quenchers include, but are not limited to, Dabcyl, Dark Quencher, Eclipse Dark Quencher, ElleQuencher, Tamra, BHQ and QSY (all of them are Trade-Marks). The skilled person would know which combinations of dye/quencher are suitable when designing a probe. In an exemplary embodiment, fluorescein (FAM) is used in conjunction with Blackhole Quencher™ (BHQ™) (Novato, Calif.). Binding of the molecular beacon to amplified product can then be directly, visually assessed. Alternatively, the fluorescence level can be measured by spectroscopy in order to improve sensitivity.

A variety of commercial suppliers produce standard and custom molecular beacons, including Abingdon Health (UK; www.abingdonhealth.com), Attostar (US, MN; www.attostar.com), Biolegio (NLD; www.biolegio.com), Biomers .net (DEU; www.biomers.net), Biosearch Technologies (US, CA; www.biosearchtech.com), Eurogentec (BEL; www.eurogentec.com), Gene Link (US, NY; www.genelink.com) Integrated DNA Technologies (US, IA;

www.idtdna.com), Isogen Life Science (NLD; www.isogenlifescience.com), Midland Certified Reagent (US, TX; www.oligos.com), Eurofins (DEU; www.eurofinsgenomics.eu), Sigma-Aldrich (US, TX; www.sigmaaldrich.com), Thermo Scientific (US, MA; www.thermoscientific.com), TIB MOLBIOL (DEU; www.tib-molbiol.de), TriLink Bio Technologies (US, CA; www.trilinkbiotech.com). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite triester method described by Beaucage and Caruthers (1981), Tetrahedron Letts. 22(20): 1859-1862, which is incorporated by reference, or another synthesis technique known in the art, e.g., using an automated synthesizer, as described in Needham-VanDevanter et al. (1984) Nucleic Acids Res. 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. To further illustrate, primers are also optionally modified to improve the specificity of amplification reactions as described in, e.g., U.S. Pat. No. 6,001,611, issued Dec. 14, 1999, which is incorporated by reference. Primers and probes can also be synthesized with various other modifications as described herein or as otherwise known in the art.

In addition, essentially any nucleic acid (and virtually any labeled nucleic acid, whether standard or non-standard) can be custom or standard ordered from any of a variety of commercial sources, such as Integrated DNA Technologies, the Midland Certified Reagent Company, Eurofins, Biosearch Technologies, Sigma Aldrich and many others.

Test samples are generally derived or isolated from subjects, typically mammalian subjects, more typically human subjects, suspected of having a *Chlamydia* infection. Exemplary samples or specimens include blood, plasma, serum, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like. Essentially any technique for acquiring these samples is optionally utilized including, e.g., scraping, venipuncture, swabbing, biopsy, or other techniques known in the art.

The term "test sample" as used herein, means a sample taken from an organism or biological fluid that is suspected of containing or potentially contains a target sequence. The test sample can be taken from any biological source, such as for example, tissue, blood, saliva, sputa, mucus, sweat, urine, urethral swabs, cervical swabs, vaginal swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

Advantageously, the invention enables reliable rapid detection of *Chlamydia trachomatis* in a clinical sample, such as a urine sample.

To further illustrate, prior to analyzing the target nucleic acids described herein, those nucleic acids may be purified or isolated from samples that typically include complex mixtures of different components. Cells in collected samples are typically lysed to release the cell contents. For example, *C. trachomatis* and other cells in the particular sample can be lysed by contacting them with various enzymes, chemicals, and/or lysed by other approaches known in the art, which degrade, e.g., bacterial cell walls. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809, which are each incorporated by reference.

A test sample may optionally have been treated and/or purified according to any technique known by the skilled person, to improve the amplification efficiency and/or qualitative accuracy and/or quantitative accuracy. The sample may thus exclusively, or essentially, consist of nucleic acid(s), whether obtained by purification, isolation, or by chemical synthesis. Means are available to the skilled person, who would like to isolate or purify nucleic acids, such as DNA, from a test sample, for example to isolate or purify DNA from cervical scrapes (e.g., QIAamp-DNA Mini-Kit; Qiagen, Hilden, Germany).

EXAMPLES

Example 1: Target Selection and Primer Probe Design

Considering the constitutive and high level of expression of the ribosomal genes in bacterial cells, these genes were chosen as targets for the amplification assay, specifically the 16S and 23S genes.

16S and 23S gene sequences for multiple serovars of *C. trachomatis*, closely related species such as *Chlamydophila pneumoniae* and *Chlamydia psittaci*, and for other species commonly found in the urine or vaginal fluid were retrieved from the NCBI database. Sequences were aligned using Clustal omega (Sievers, et al. 2011. Molecular Systems Biology 7:539) and regions with unique specific bases to *C. trachomatis* species were identified. Loop mediated amplification primers were designed using LAMP designer (Premier Biosoft). For added specificity, molecular beacons or probes targeting the amplified products were designed manually or using Beacon designer (Premier Biosoft). Designed primer sets and beacons were further analyzed for specificity using BLAST against the human genome and the NCBI nucleotide database. Various primer sets and probes were designed and screened for reaction speed.

The inventive primer sets are summarized in Table 2, which include, at a minimum, a forward inner primer (FIP) and backward inner primer (BIP). Additionally, the primer sets typically also include at least two additional primers selected from the forward outer primer (F3), backward outer primer (B3), forward loop primer (LF) and backward loop primer (LB).

TABLE 2

LAMP Primer Sets

| Set | F3 | B3 | FIP | BIP | LF | LB |
|---|---|---|---|---|---|---|
| Set-1 | SEQ ID NO: 1 | SEQ ID NO: 2 | SEQ ID NO: 3 | SEQ ID NO: 4 | SEQ ID NO: 5 | SEQ ID NO: 6 |
| Set-2 | SEQ ID NO: 7 | SEQ ID NO: 8 | SEQ ID NO: 9 | SEQ ID NO: 10 | SEQ ID NO: 11 | SEQ ID NO: 12 |
| Set-3 | SEQ ID NO: 13 | SEQ ID NO: 14 | SEQ ID NO: 15 | SEQ ID NO: 16 | SEQ ID NO: 17 | SEQ ID NO: 18 |
| Set-4 | SEQ ID NO: 19 | SEQ ID NO: 20 | SEQ ID NO: 21 | SEQ ID NO: 22 | SEQ ID NO: 23 | SEQ ID NO: 24 |
| Set-5 | SEQ ID NO: 25 | SEQ ID NO: 26 | SEQ ID NO: 27 | SEQ ID NO: 28 | SEQ ID NO: 29 | SEQ ID NO: 30 |
| Set-6 | SEQ ID NO: 31 | SEQ ID NO: 32 | SEQ ID NO: 33 | SEQ ID NO: 34 | SEQ ID NO: 35 | SEQ ID NO: 36 |
| Set-7 | SEQ ID NO: 37 | SEQ ID NO: 38 | SEQ ID NO: 39 | SEQ ID NO: 40 | SEQ ID NO: 41 | SEQ ID NO: 42 |
| Set-8 | SEQ ID NO: 43 | SEQ ID NO: 44 | SEQ ID NO: 45 | SEQ ID NO: 46 | SEQ ID NO: 47 | SEQ ID NO: 48 |
| Set-9 | SEQ ID NO: 49 | SEQ ID NO: 52 | SEQ ID NO: 50 | SEQ ID NO: 53 | SEQ ID NO: 51 | SEQ ID NO: 54 |
| Set-10 | SEQ ID NO: 55 | SEQ ID NO: 58 | SEQ ID NO: 56 | SEQ ID NO: 59 | SEQ ID NO: 57 | SEQ ID NO: 60 |
| Set-11 | SEQ ID NO: 49 | SEQ ID NO: 62 | SEQ ID NO: 61 | SEQ ID NO: 53 | SEQ ID NO: 51 | SEQ ID NO: 63 |
| Set-12 | SEQ ID NO: 64 | SEQ ID NO: 65 | SEQ ID NO: 66 | SEQ ID NO: 67 | SEQ ID NO: 68 | SEQ ID NO: 69 |
| Set-13 | SEQ ID NO: 70 | SEQ ID NO: 71 | SEQ ID NO: 72 | SEQ ID NO: 73 | SEQ ID NO: 74 | SEQ ID NO: 75 |
| Set-14 | SEQ ID NO: 81 | SEQ ID NO: 82 | SEQ ID NO: 83 | SEQ ID NO: 84 | SEQ ID NO: 76 | SEQ ID NO: 86 |
| Set-15 | SEQ ID NO: 81 | SEQ ID NO: 82 | SEQ ID NO: 83 | SEQ ID NO: 84 | SEQ ID NO: 77 | SEQ ID NO: 86 |
| Set-16 | SEQ ID NO: 81 | SEQ ID NO: 82 | SEQ ID NO: 83 | SEQ ID NO: 84 | SEQ ID NO: 78 | SEQ ID NO: 86 |
| Set-17 | SEQ ID NO: 81 | SEQ ID NO: 82 | SEQ ID NO: 83 | SEQ ID NO: 84 | SEQ ID NO: 79 | SEQ ID NO: 86 |
| Set-18 | SEQ ID NO: 81 | SEQ ID NO: 82 | SEQ ID NO: 83 | SEQ ID NO: 84 | SEQ ID NO: 80 | SEQ ID NO: 86 |
| Set-19 | SEQ ID NO: 87 | SEQ ID NO: 82 | SEQ ID NO: 89 | SEQ ID NO: 84 | SEQ ID NO: 91 | SEQ ID NO: 86 |
| Set-20 | SEQ ID NO: 81 | SEQ ID NO: 82 | SEQ ID NO: 83 | SEQ ID NO: 84 | SEQ ID NO: 85 | SEQ ID NO: 86 |
| Set-21 | SEQ ID NO: 87 | SEQ ID NO: 88 | SEQ ID NO: 89 | SEQ ID NO: 90 | SEQ ID NO: 91 | SEQ ID NO: 92 |
| Set-22 | SEQ ID NO: 87 | SEQ ID NO: 82 | SEQ ID NO: 89 | SEQ ID NO: 84 | SEQ ID NO: 76 | SEQ ID NO: 86 |
| Set-23 | SEQ ID NO: 87 | SEQ ID NO: 82 | SEQ ID NO: 93 | SEQ ID NO: 84 | SEQ ID NO: 76 | SEQ ID NO: 86 |
| Set-24 | SEQ ID NO: 87 | SEQ ID NO: 82 | SEQ ID NO: 94 | SEQ ID NO: 84 | SEQ ID NO: 76 | SEQ ID NO: 86 |
| Set-25 | SEQ ID NO: 87 | SEQ ID NO: 82 | SEQ ID NO: 89 | SEQ ID NO: 95 | SEQ ID NO: 91 | SEQ ID NO: 92 |
| Set-26 | SEQ ID NO: 87 | SEQ ID NO: 82 | SEQ ID NO: 93 | SEQ ID NO: 95 | SEQ ID NO: 76 | SEQ ID NO: 92 |
| Set-27 | SEQ ID NO: 87 | SEQ ID NO: 82 | SEQ ID NO: 94 | SEQ ID NO: 95 | SEQ ID NO: 76 | SEQ ID NO: 92 |
| Set-28 | SEQ ID NO: 1 | SEQ ID NO: 2 | SEQ ID NO: 3 | SEQ ID NO: 4 | — | — |
| Set-29 | SEQ ID NO: 7 | SEQ ID NO: 8 | SEQ ID NO: 9 | SEQ ID NO: 10 | — | — |
| Set-30 | SEQ ID NO: 13 | SEQ ID NO: 14 | SEQ ID NO: 15 | SEQ ID NO: 16 | — | — |
| Set-31 | SEQ ID NO: 19 | SEQ ID NO: 20 | SEQ ID NO: 21 | SEQ ID NO: 22 | — | — |
| Set-32 | SEQ ID NO: 25 | SEQ ID NO: 26 | SEQ ID NO: 27 | SEQ ID NO: 28 | — | — |
| Set-33 | SEQ ID NO: 31 | SEQ ID NO: 32 | SEQ ID NO: 33 | SEQ ID NO: 34 | — | — |
| Set-34 | SEQ ID NO: 37 | SEQ ID NO: 38 | SEQ ID NO: 39 | SEQ ID NO: 40 | — | — |
| Set-35 | SEQ ID NO: 43 | SEQ ID NO: 44 | SEQ ID NO: 45 | SEQ ID NO: 46 | — | — |
| Set-36 | SEQ ID NO: 49 | SEQ ID NO: 52 | SEQ ID NO: 50 | SEQ ID NO: 53 | — | — |
| Set-37 | SEQ ID NO: 55 | SEQ ID NO: 58 | SEQ ID NO: 56 | SEQ ID NO: 59 | — | — |
| Set-38 | SEQ ID NO: 49 | SEQ ID NO: 62 | SEQ ID NO: 61 | SEQ ID NO: 53 | — | — |
| Set-39 | SEQ ID NO: 64 | SEQ ID NO: 65 | SEQ ID NO: 66 | SEQ ID NO: 67 | — | — |
| Set-40 | SEQ ID NO: 70 | SEQ ID NO: 71 | SEQ ID NO: 72 | SEQ ID NO: 73 | — | — |
| Set-41 | SEQ ID NO: 81 | SEQ ID NO: 82 | SEQ ID NO: 83 | SEQ ID NO: 84 | — | — |
| Set-42 | SEQ ID NO: 81 | SEQ ID NO: 82 | SEQ ID NO: 83 | SEQ ID NO: 84 | — | — |
| Set-43 | SEQ ID NO: 81 | SEQ ID NO: 82 | SEQ ID NO: 83 | SEQ ID NO: 84 | — | — |
| Set-44 | SEQ ID NO: 81 | SEQ ID NO: 82 | SEQ ID NO: 83 | SEQ ID NO: 84 | — | — |
| Set-45 | SEQ ID NO: 81 | SEQ ID NO: 82 | SEQ ID NO: 83 | SEQ ID NO: 84 | — | — |
| Set-46 | SEQ ID NO: 87 | SEQ ID NO: 82 | SEQ ID NO: 89 | SEQ ID NO: 84 | — | — |
| Set-47 | SEQ ID NO: 81 | SEQ ID NO: 82 | SEQ ID NO: 83 | SEQ ID NO: 84 | — | — |
| Set-48 | SEQ ID NO: 87 | SEQ ID NO: 88 | SEQ ID NO: 89 | SEQ ID NO: 90 | — | — |
| Set-49 | SEQ ID NO: 87 | SEQ ID NO: 82 | SEQ ID NO: 89 | SEQ ID NO: 84 | — | — |
| Set-50 | SEQ ID NO: 87 | SEQ ID NO: 82 | SEQ ID NO: 93 | SEQ ID NO: 84 | — | — |
| Set-51 | SEQ ID NO: 87 | SEQ ID NO: 82 | SEQ ID NO: 94 | SEQ ID NO: 84 | — | — |
| Set-52 | SEQ ID NO: 87 | SEQ ID NO: 82 | SEQ ID NO: 89 | SEQ ID NO: 95 | — | — |
| Set-53 | SEQ ID NO: 87 | SEQ ID NO: 82 | SEQ ID NO: 93 | SEQ ID NO: 95 | — | — |
| Set-54 | SEQ ID NO: 87 | SEQ ID NO: 82 | SEQ ID NO: 94 | SEQ ID NO: 95 | — | — |
| Set-55 | — | — | SEQ ID NO: 3 | SEQ ID NO: 4 | — | — |
| Set-56 | — | — | SEQ ID NO: 9 | SEQ ID NO: 10 | — | — |
| Set-57 | — | — | SEQ ID NO: 15 | SEQ ID NO: 16 | — | — |
| Set-58 | — | — | SEQ ID NO: 21 | SEQ ID NO: 22 | — | — |
| Set-59 | — | — | SEQ ID NO: 27 | SEQ ID NO: 28 | — | — |
| Set-60 | — | — | SEQ ID NO: 33 | SEQ ID NO: 34 | — | — |
| Set-61 | — | — | SEQ ID NO: 39 | SEQ ID NO: 40 | — | — |
| Set-62 | — | — | SEQ ID NO: 45 | SEQ ID NO: 46 | — | — |
| Set-63 | — | — | SEQ ID NO: 50 | SEQ ID NO: 53 | — | — |
| Set-64 | — | — | SEQ ID NO: 56 | SEQ ID NO: 59 | — | — |
| Set-65 | — | — | SEQ ID NO: 61 | SEQ ID NO: 53 | — | — |
| Set-66 | — | — | SEQ ID NO: 66 | SEQ ID NO: 67 | — | — |

TABLE 2-continued

LAMP Primer Sets

| Set | F3 | B3 | FIP | BIP | LF | LB |
|---|---|---|---|---|---|---|
| Set-67 | — | — | SEQ ID NO: 72 | SEQ ID NO: 73 | — | — |
| Set-68 | — | — | SEQ ID NO: 83 | SEQ ID NO: 84 | — | — |
| Set-69 | — | — | SEQ ID NO: 83 | SEQ ID NO: 84 | — | — |
| Set-70 | — | — | SEQ ID NO: 83 | SEQ ID NO: 84 | — | — |
| Set-71 | — | — | SEQ ID NO: 83 | SEQ ID NO: 84 | — | — |
| Set-72 | — | — | SEQ ID NO: 83 | SEQ ID NO: 84 | — | — |
| Set-73 | — | — | SEQ ID NO: 89 | SEQ ID NO: 84 | — | — |
| Set-74 | — | — | SEQ ID NO: 83 | SEQ ID NO: 84 | — | — |
| Set-75 | — | — | SEQ ID NO: 89 | SEQ ID NO: 90 | — | — |
| Set-76 | — | — | SEQ ID NO: 89 | SEQ ID NO: 84 | — | — |
| Set-77 | — | — | SEQ ID NO: 93 | SEQ ID NO: 84 | — | — |
| Set-78 | — | — | SEQ ID NO: 94 | SEQ ID NO: 84 | — | — |
| Set-79 | — | — | SEQ ID NO: 89 | SEQ ID NO: 95 | — | — |
| Set-80 | — | — | SEQ ID NO: 93 | SEQ ID NO: 95 | — | — |
| Set-81 | — | — | SEQ ID NO: 94 | SEQ ID NO: 95 | — | — |

Example 2: Amplification Reaction Kinetics

A negative urine matrix was spiked with titred *C. trachomatis* (strain Z054, D-UW3 (Zeptometrix) or ATCC serovar D strain VR-885) at two different concentrations ($10^3$ IFU/mL and 10 IFU/mL). Nucleic acids were extracted using standard extraction methods and the sample was amplified using LAMP primers sets as described in Table 2. YoPro™ dye (Life Technologies; green fluorescent carbocyanine nucleic acid stain) was used for the detection of the amplified product. In this example a 25 µl reaction contained 1× Isothermal Amplification Buffer (New England Biolabs) supplemented with 4.8 mM or 6 mM MgCl2, 1.4 mM or 1.6 mM dNTP, 200 nM YO-PRO-1 dye (Life Technologies), primers (0.2 µM of F3 and B3, when present; 1.6 µM of FIP and BIP; 0.4-0.8 µM of LF and LB, when present), 8 or 12 Units of Bst2 polymerase (New England Biolabs), 7.5 Units RTx Warmstart (reverse transcriptase; New England Biolabs), and the extracted nucleic acid (as template) or water (as no template control). The reactions were incubated at 63° or 65° C. and kinetics were monitored using a Roche real-time Lightcycler96 (Roche).

This example shows that using this set of primers and the loop mediated amplification method, fast amplification kinetics are achieved. Results are summarized in Table 3, in which the Time to Positive (Tp) was calculated by the instrument. NT indicates concentrations not tested. Results are classified by the time to positive (NT means "not tested" and "no call" indicates that no amplification was detected).

TABLE 3

Time to Positive Dye Detection

| primers | $T_p$ $10^3$IFU/mL | $T_p$ 10 IFU/mL | NTC |
|---|---|---|---|
| Set-1 | 6.1 | 7.8 | 25.12 |
| Set-2 | 8.6 | 10.8 | 36.81 |
| Set-3 | 6.6 | 9.1 | 28.59 |
| Set-4 | 8.2 | 19.8 | 36.77 |
| Set-5 | 7.9 | 11.1 | 31.42 |
| Set-6 | 8.8 | 12.2 | 38.28 |
| Set-7 | 11.0 | 14.4 | 21.05 |
| Set-8 | 10.9 | 14.2 | 19.86 |
| Set-9 | NT | 7.0 | 42.89 |
| Set-10 | NT | 6.8 | 32.68 |
| Set-11 | NT | 11.0 | 27.34 |
| Set-12 | 4.1 | 6.54 | 48.03 |
| Set-13 | 7.3 | 10.13 | 46.55 |
| Set-14 | 4.4 | 5.18 | 29.24 |
| Set-15 | 4.6 | 5.21 | 20.34 |
| Set-16 | 4.6 | 5.40 | 43.24 |
| Set-17 | 4.5 | 5.36 | 23.37 |
| Set-18 | 3.9 | 6.00 | 23.78 |

Example 3: Beacon Design Location Effect on Assay Kinetics

Amplification reactions containing some of the above primers sets and the intercalating dye resulted in the detection of an amplification product when using water or negative urine extraction or the DNA of closely related specie such as *C. pneumoniae* or *C. psittaci* as templates at frequencies ranging between 0% to 75% of the time (Table 4), within variable intervals of our cut off window for the assay time. Results are classified by the time to positive ("no call" indicates that no amplification was detected).

TABLE 4

Cross Reactivity - Dye Detection

| Primer Set | NTC (water) | | C. pneumoniae DNA | | C. psittaci DNA | |
|---|---|---|---|---|---|---|
| Set-9 | 42.9 | 1 of 2 | 15.2 | 1 of 1 | NT | — |
| Set-10 | 32.7 | 1 of 2 | 9.4 | 1 of 1 | NT | — |
| Set-11 | 27.3 | 1 of 2 | 18.0 | 1 of 1 | NT | — |

For added specificity molecular beacons were designed along these primers sets to make sure only signal from the *C. trachomatis* target is detected (sequences listed in table 5). Each molecular beacon probe was designed with 5' fluorophore/3' quencher modifications (6-Carboxyfluorescein (FAM) and Black Hole Quencher 1 (BHQ1)) included to provide target-specific fluorescent detection.

TABLE 5

| ID | Fluor | Quench | Sequence (5' to 3') | Sequence ID |
|---|---|---|---|---|
| MB1 | FAM | BHQ1 | CGCGCACATCTGGAAAGATGGATGATACAGGGTGCGCG | SEQ ID NO: 97 |
| MB2 | FAM | BHQ1 | CGTCCAGGACTCCTAGTTGAACACATCTGGACG | SEQ ID NO: 98 |
| MB3 | FAM | BHQ1 | CCGGATCAGGACTCCTAGTTGAACACATCTGATCCGG | SEQ ID NO: 99 |
| MB4 | FAM | BHQ1 | CGGCCAGGACTCCTAGTTGAACACATCTGGCCG | SEQ ID NO: 100 |
| MB5 | FAM | BHQ1 | CGTCCGGATCAGGACTCCTAGTTGAACACCGGACG | SEQ ID NO: 101 |
| MB6 | FAM | BHQ1 | CTCGCCACGTGAAACCTAGTCTGAATCTGGCGAG | SEQ ID NO: 102 |
| MB7 | FAM | BHQ1 | CCGTGGATGATACAGGGTGATAGTCCACGG | SEQ ID NO: 103 |
| MB8 | FAM | BHQ1 | CGTGGGATGATACAGGGTGATAGTCCCCACG | SEQ ID NO: 104 |
| MB9 | FAM | BHQ1 | CGGCTCGAGATTCCCTGTGTAGCGGCGAGCCG | SEQ ID NO: 105 |
| MB10 | FAM | BHQ1 | CGCCAGGATCAGGACTCCTAGTTGAACCTGGCG | SEQ ID NO: 106 |
| MB11 | FAM | BHQ1 | CACCGGGATGATACAGGGTGATAGTCCCGGTC | SEQ ID NO: 107 |
| MB12 | FAM | BHQ1 | CACCGGGATGATACAGGGTGATAGTCCCGGTG | SEQ ID NO: 108 |
| MB13 | FAM | BHQ1 | TCGCGGGATGATACAGGGTGATAGTCCCGCGG | SEQ ID NO: 109 |
| MB14 | FAM | BHQ1 | CAGCGGGATCAGGACTCCTAGTTGAACCCGCTG | SEQ ID NO: 110 |
| MB15 | FAM | BHQ1 | CACGCTCGAGATTCCCTGTGTAGCGGCGAGCGTG | SEQ ID NO: 111 |
| MB16 | FAM | BHQ1 | CAGGCGGATCAGGACTCCTAGTTGAACACCGCCTG | SEQ ID NO: 112 |
| MB17 | FAM | BHQ1 | CAGCGACAGAAATCGAAGAGATTCCCTGTGTCGCTG | SEQ ID NO: 113 |
| MB18 | FAM | BHQ1 | CACGGGATGATACAGGGTGATAGTCCCGTC | SEQ ID NO: 114 |
| MB19 | FAM | BHQ1 | CACGGGATGATACAGGGTGATAGTCCCGTG | SEQ ID NO: 115 |
| MB20 | FAM | BHQ1 | CACGATGGATGATACAGGGTGATAGTCCATCGTG | SEQ ID NO: 116 |
| MB21 | FAM | BHQ1 | CACCGATGGATGATACAGGGTGATAGTCCCATCGGTG | SEQ ID NO: 117 |
| MB22 | FAM | BHQ1 | CGCGATCGAGGATAAAGGATCAGGACTCGATCGCG | SEQ ID NO: 118 |
| MB23 | FAM | BHQ1 | CGCGATCATTGAGGATAAAGGATCAGGACTGATCGCG | SEQ ID NO: 119 |
| MB24 | FAM | BHQ1 | CGCGATCCTCCTAGTTGAACACATCTGGAGATCGCG | SEQ ID NO: 120 |
| MB25 | FAM | BHQ1 | CGCGATCAGGACTCCTAGTTGAACACATCTGGATCGCG | SEQ ID NO: 121 |
| MB26 | FAM | BHQ1 | CGCGACTCAGGACTCCTAGTTGAACACATCTGGAGTCGCG | SEQ ID NO: 122 |
| MB27 | FAM | BHQ1 | CGCGATCCGGATAAAGGATCAGGACTCCTAGTTGGGATCGCG | SEQ ID NO: 123 |
| MB28 | FAM | BHQ1 | CGCGAGTAGGATTGAGGATAAAGGATCAGGACTCGCG | SEQ ID NO: 124 |
| MB29 | FAM | BHQ1 | CGCGATCCCTGTGTAGCGGCGAGCGAGATCGCG | SEQ ID NO: 125 |
| MB30 | FAM | BHQ1 | CGCGATCCTGTGTAGCGGCGAGCGAAAGATCGCG | SEQ ID NO: 126 |
| MB31 | FAM | BHQ1 | CGGCTCGGGGTTGTAGGATTGAGGATACGAGCCG | SEQ ID NO: 127 |
| MB32 | FAM | BHQ1 | CCGGAGCCTACAACCCCGAGCCTTATCAGCTCCGG | SEQ ID NO: 128 |
| MB33 | FAM | BHQ1 | GCGCAGCTCGGTTTAGGCTATTCCCCTGCGCG | SEQ ID NO: 129 |
| MB34 | FAM | BHQ1 | CGCGGTCTCTCCTTTCGTCTACGGGACCGCG | SEQ ID NO: 130 |
| MB35 | FAM | BHQ1 | CGCAGTGAGAGAAAGACCGACCTCAACACTGCG | SEQ ID NO: 131 |

A negative urine matrix was spiked with titred *C. trachomatis* (strain Z054, D-UW3 (Zeptometrix) or ATCC serovar D strain VR-885) at two different concentrations ($10^3$ IFU/mL and 10 IFU/mL). Nucleic acids were extracted using standard extraction methods and the sample was amplified using a LAMP primer set (per Table 2) and one of the molecular beacons (per Table 4) was used for the detection of the amplified product. In this example a 25 µl reaction contained 1× Isothermal Amplification Buffer (New England Biolabs) supplemented with 4.8 mM or 6 mM MgCl2, 1.4 mM or 1.6 mM dNTP, 200 nM molecular beacon (Sigma-Aldrich), primers (0.2 µM of F3 and B3, if present; 1.6 µM or 2 µM of FIP and BIP; 0.4-0.8 µM of LF and LB, if present), 8 or 12 Units of Bst2 polymerase (New England Biolabs), 7.5 Units RTx Warmstart (reverse transcriptase; New England Biolabs), and the extracted nucleic acid (as template) or water (as no template control). The reactions were incubated at 63° C. and kinetics were monitored using a Roche real-time Lightcycler96 (Roche). The time to positive for each primer-probe combination is reported in Table 6. Results are classified by the time to positive (Tp) from reaction initiation as follows: "NT" indicates that this combination was not tested and "no call" indicates that no amplification was detected.

TABLE 6

Time to Positive Probe Detection

| Primers | Beacon | $10^3$ IFU/mL | 10 1FU/mL | NTC |
|---|---|---|---|---|
| Set-12 | MB1 | 5.6 | 7.6 | no call |
| Set-12 | MB2 | 4.8 | 6.7 | no call |
| Set-12 | MB3 | 5.2 | 7.2 | no call |
| Set-12 | MB4 | 6.3 | 8.4 | no call |
| Set-12 | MB5 | 5.6 | 7.4 | no call |
| Set-13 | MB2 | 14.6 | 20.9 | no call |
| Set-13 | MB6 | 8.9 | 11.2 | no call |
| Set-14 | MB11 | 4.8 | 6.7 | no call |
| Set-14 | MB12 | 5.2 | 6.7 | no call |
| Set-14 | MB13 | 5.1 | 6.9 | no call |
| Set-14 | MB15 | 5.5 | 7.0 | no call |
| Set-14 | MB18 | 4.8 | 6.5 | no call |
| Set-14 | MB19 | 5.8 | 7.3 | no call |
| Set-14 | MB2 | 4.9 | 6.5 | no call |
| Set-14 | MB7 | 4.8 | 6.3 | no call |
| Set-14 | MB8 | 4.9 | 6.7 | no call |
| Set-14 | MB9 | 5.2 | 7.0 | no call |
| Set-15 | MB2 | 4.4 | 6.4 | no call |
| Set-16 | MB2 | 4.2 | 7.4 | no call |
| Set-17 | MB2 | 4.3 | 6.0 | no call |
| Set-18 | MB2 | 4.8 | 6.6 | no call |
| Set-19 | MB11 | 6.0 | 8.0 | no call |
| Set-19 | MB12 | 5.9 | 7.9 | no call |
| Set-19 | MB13 | 5.9 | 8.0 | no call |
| Set-19 | MB18 | 5.6 | 7.4 | no call |
| Set-19 | MB19 | 6.6 | 8.7 | no call |
| Set-19 | MB2 | 4.7 | 6.6 | no call |
| Set-19 | MB20 | 5.7 | 7.7 | no call |

TABLE 6-continued

Time to Positive Probe Detection

| Primers | Beacon | $10^3$ IFU/mL | 10 1FU/mL | NTC |
|---|---|---|---|---|
| Set-19 | MB21 | 5.7 | 7.6 | no call |
| Set-20 | MB11 | 5.2 | 7.3 | no call |
| Set-20 | MB12 | 5.2 | 6.7 | no call |
| Set-20 | MB13 | 4.9 | 6.7 | no call |
| Set-20 | MB15 | 5.1 | 7.2 | no call |
| Set-20 | MB18 | 4.7 | 6.7 | no call |
| Set-20 | MB19 | 5.5 | 7.3 | no call |
| Set-20 | MB20 | 5.6 | 7.2 | no call |
| Set-20 | MB21 | 5.1 | 7.2 | no call |
| Set-20 | MB3 | 5.8 | 7.7 | no call |
| Set-20 | MB4 | 5.0 | 6.7 | 32.7 |
| Set-20 | MB7 | 5.0 | 6.8 | no call |
| Set-20 | MB8 | 5.0 | 6.9 | no call |
| Set-20 | MB9 | 4.9 | 7.1 | no call |
| Set-21 | MB10 | 6.8 | 8.5 | no call |
| Set-21 | MB14 | 6.7 | 8.9 | no call |
| Set-21 | MB16 | 6.4 | 8.4 | no call |
| Set-21 | MB17 | 2.7 | 3.5 | no call |
| Set-21 | MB3 | 8.2 | 10.3 | no call |
| Set-21 | MB4 | 6.9 | 8.9 | no call |
| Set-22 | MB19 | 7.3 | 9.3 | no call |
| Set-23 | MB19 | 11.8 | 14.8 | no call |
| Set-24 | MB19 | 6.5 | 8.4 | no call |
| Set-24 | MB20 | 6.3 | 8.3 | no call |
| Set-24 | MB21 | 5.9 | 8.1 | no call |
| Set-25 | MB19 | 7.3 | 9.7 | no call |
| Set-25 | MB20 | 7.6 | 10.0 | no call |
| Set-25 | MB21 | 7.2 | 8.4 | no call |
| Set-26 | MB19 | 19.0 | 25.5 | 41.4 |
| Set-27 | MB19 | 7.9 | 10.0 | no call |
| Set-76 | MB19 | 17.3 | NT | no call |
| Set-78 | MB19 | 12.2 | NT | no call |
| Set-79 | MB19 | 28.6 | NT | no call |
| Set-81 | MB19 | 22.1 | NT | no call |

Use of Molecular Beacons for detection resulted in a slight increase in reaction Tp, however the significant enhancement in assay specificity provided a reasonable tradeoff, no amplification was observed in the water sample or DNA from a close related species within the testing period of 45 min (see Example 4, Table 7).

Example 4: Specificity Testing

A negative urine matrix was spiked with titred *C. trachomatis* or with organisms commonly associated with sexually transmitted infections (e.g., *Neisseria gonorrhoeae*) or species closely related to *C. trachomatis* (*C. pneumonia* or *C. psittaci*). Bacterial stocks were serially diluted in PBS before addition to the urine matrix at the desired concentration. Corresponding extracted nucleic acids or DNAs of the test species were used as templates in RT-LAMP reactions containing the LAMP primers and molecular beacon probe, according to the methods described Example 3, above. NT indicates reactions not tested.

TABLE 7

Cross Reactivity - Probe Detection

| Primers | Beacon | $10^3$ IFU/mL | 10 IFU/mL | *C. pneumoniae* | *C. psittaci* | *N. gonorrhoeae* | NTC |
|---|---|---|---|---|---|---|---|
| Set-14 | MB2 | 4.4 | 6.2 | 13.5 | 13.2 | 20.2 | 19.6 |
| Set-14 | MB11 | NT | 6.7 | 18.6 | 14.4 | 32.1 | 23.3 |
| Set-20 | MB2 | 4.7 | 7.0 | 22.5 | 23.5 | 21.8 | 21.1 |
| Set-20 | MB11 | NT | 6.7 | 26.4 | 27.1 | 27.8 | 20.4 |
| Set-21 | MB2 | 6.6 | 8.6 | No call | No call | No call | No call |
| Set-19 | MB19 | NT | 8.1 | No call | No call | No call | No call |

TABLE 7-continued

Cross Reactivity - Probe Detection

| Primers | Beacon | 10³ IFU/mL | 10 IFU/mL | C. pneumoniae | C. psittaci | N. gonorrhoeae | NTC |
|---|---|---|---|---|---|---|---|
| Set-20 | MB19 | NT | 7.8 | 33.4 | 28.6 | No call | No call |
| Set-14 | MB19 | NT | 7.3 | 20.1 | 14.9 | No call | No call |

This example shows that the CT23S assay and its reaction formulation can be designed to be highly specific, limiting cross reactivity with sequences of closely related organisms and those commonly associated with sexually transmitted infections.

Example 5: Sensitivity Testing

A RNA molecular standard was diluted to various concentrations to assess the sensitivity of the indicated primer set/molecular beacon combinations (Table 8). Standards were serially diluted with 0.1 mg/mL Poly A carrier RNA in PBS (Sigma) and used as template for amplification in RTLAMP reactions. Final concentrations in reactions were 40, 8, or 4 copies/uL. Reaction conditions were equivalent to those described above in Example 3. Amplification signal was obtained with concentrations as low as 4 copies/uL (see Table 8).

TABLE 8

Sensitivity with LAMP and Molecular Beacon

| Primer Set | Beacon | 40 copies/uL | 8 copies/uL | 4 copies/uL |
|---|---|---|---|---|
| Set-14 | MB2 | 6.5 | 7.6 | 12.3 |
| Set-20 | MB2 | 6.5 | 7.8 | 9.9 |

We claim:

1. A composition comprising a set of primers selected from the group consisting of:
   i. a primer set comprising a forward outer primer comprising SEQ ID NO: 87, a backward outer primer comprising SEQ ID NO: 82, a forward inner primer comprising SEQ ID NO: 94, a backward inner primer comprising SEQ ID NO: 84, a forward loop primer comprising SEQ ID NO: 76, and a backward loop primer comprising SEQ ID NO: 86;
   ii. a primer set comprising a forward outer primer comprising SEQ ID NO: 87, a backward outer primer comprising SEQ ID NO: 82, a forward inner primer comprising SEQ ID NO: 94, and a backward inner primer comprising SEQ ID NO: 84; and
   iii. a primer set comprising a forward inner primer comprising SEQ ID NO: 94 and a backward inner primer comprising SEQ ID NO: 84.

2. The composition of claim 1, further comprising a probe.

3. The composition of claim 2, wherein the probe is a labeled polynucleotide.

4. The composition of claim 3, wherein the labeled polynucleotide comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, and nucleotides 6-27 of SEQ ID NO: 130.

5. The composition of claim 2, wherein the probe is a molecular beacon comprising a fluorophore, a quencher, and a polynucleotide.

6. The composition of claim 5, wherein the molecular beacon comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, and nucleotides 6-27 of SEQ ID NO: 130.

7. The composition of claim 6, wherein the molecular beacon comprises a sequence selected from the group consisting of SEQ ID NOs: 97-101 and 103-130.

8. The composition of claim 7, wherein the polynucleotide sequence consists of SEQ ID NO: 115.

9. A kit comprising a composition according to claim 1.

10. The kit of claim 9, further comprising a strand displacement polymerase.

11. The kit of claim 9, further comprising a molecular beacon comprising a fluorophore, a quencher, and a polynucleotide, wherein the polynucleotide consists of a sequence selected from the group consisting of SEQ ID NOs: 97-101 and 103-130.

12. The kit of claim 11, wherein the polynucleotide consists of SEQ ID NO: 115.

13. The composition of claim 1, wherein the set of primers is selected from the group consisting of:
   i. a primer set consisting of a forward outer primer consisting essentially of SEQ ID NO: 87, a backward outer primer consisting essentially of SEQ ID NO: 82, a forward inner primer consisting essentially of SEQ ID NO: 94, a backward inner primer consisting essentially of SEQ ID NO: 84, a forward loop primer consisting essentially of SEQ ID NO: 76, and a backward loop primer consisting essentially of SEQ ID NO: 86;
   ii. a primer set consisting of a forward outer primer consisting essentially of SEQ ID NO: 87, a backward outer primer consisting essentially of SEQ ID NO: 82, a forward inner primer consisting essentially of SEQ ID NO: 94, and a backward inner primer consisting essentially of SEQ ID NO: 84; and
   iii. a primer set consisting of a forward inner primer consisting essentially of SEQ ID NO: 94 and a backward inner primer consisting essentially of SEQ ID NO: 84.

14. A method of detecting *Chlamydia trachomatis* in a test sample, the method comprising:
   (a) extracting nucleic acid from the test sample;
   (b) amplifying a target sequence by reacting the nucleic acid extracted in step (a) with a reaction mixture comprising a strand displacement DNA polymerase and a sequence-specific primer set, wherein said sequence-specific primer set is selected from the group consisting of:
   (i) a primer set comprising a forward outer primer comprising SEQ ID NO: 87, a backward outer primer comprising SEQ ID NO: 82, a forward inner primer comprising SEQ ID NO: 94, a backward inner primer comprising SEQ ID NO: 84, a forward loop primer comprising SEQ ID NO: 76, and a backward loop primer comprising SEQ ID NO: 86;
   (ii) a primer set comprising a forward outer primer comprising SEQ ID NO: 87, a backward outer primer comprising SEQ ID NO: 82, a forward inner primer comprising SEQ ID NO: 94, and a backward inner primer comprising SEQ ID NO: 84; and
   (iii) a primer set comprising a forward inner primer comprising SEQ ID NO: 94 and a backward inner primer comprising SEQ ID NO: 84; and (c) detecting the presence or absence of an amplified product of step (b); wherein the presence of said amplification product is indicative of the presence of *Chlamydia trachomatis* in the test sample.

15. The method of claim 14, wherein the amplification in step (b) of the target sequence is performed at between about 60° C. and about 67° C. for less than fifteen minutes.

16. The method of claim 15, wherein the amplification step is performed for less than ten minutes.

17. The method of claim 14, wherein the reaction mixture further comprises a reverse transcriptase.

18. The method of claim 14, wherein detecting the presence or absence of the amplification product comprises hybridizing the amplified product with a probe comprising a polynucleotide attached to a label.

19. The method of claim 18, wherein the labeled polynucleotide comprises a sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO:119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, and nucleotides 6-27 of SEQ ID NO: 130.

20. The method of claim 19, wherein the labeled polynucleotide comprises a sequence selected from the group consisting of SEQ ID NOs: 97-101 and 103-130.

21. The method of claim 20, wherein the sequence of the labeled polynucleotide is SEQ ID NO: 115.

22. The method of claim 14, wherein *Chlamydia trachomatis* is present in the test sample at a concentration of <100 IFU/mL.

23. The method of claim 22, wherein *Chlamydia trachomatis* is present in the test sample at a concentration of <5 IFU/ml and the amplification step is performed for less than 15 minutes.

24. The method of claim 22, wherein *Chlamydia trachomatis* is present in the test sample at a concentration of <10 IFU/ml and the amplification step is performed for less than six minutes.

25. A method of detecting *Chlamydia trachomatis* in a test sample, the method comprising:

(a) extracting nucleic acid from the test sample;

(b) amplifying a target sequence by reacting the nucleic acid extracted in step (a) for less than ten minutes with a reaction mixture comprising a strand displacement DNA polymerase and a sequence-specific LAMP primer set comprising a forward outer primer comprising SEQ ID NO: 87, a backward outer primer comprising SEQ ID NO: 82, a forward inner primer comprising SEQ ID NO: 94, a backward inner primer comprising SEQ ID NO: 84, a forward loop primer comprising SEQ ID NO: 76, and a backward loop primer comprising SEQ ID NO: 86; and (c) detecting the presence or absence of an amplified product of step (b); wherein the presence of said amplification product is indicative of the presence of *Chlamydia trachomatis* in the test sample.

26. The method of claim 25, wherein detecting the presence or absence of the amplification product comprises hybridizing the amplified product with a molecular beacon comprising a polynucleotide sequence selected from the group consisting of nucleotides 5-34 of SEQ ID NO: 97, nucleotides 5-31 of SEQ ID NO: 98, nucleotides 3-31 of SEQ ID NO: 99, nucleotides 5-30 of SEQ ID NO: 100, nucleotides 6-29 of SEQ ID NO: 101, nucleotides 5-26 of SEQ ID NO: 103, nucleotides 4-27 of SEQ ID NO: 104, nucleotides 7-30 of SEQ ID NO: 105, nucleotides 5-27 of SEQ ID NO: 106, nucleotides 6-29 of SEQ ID NO: 107, nucleotides 6-29 of SEQ ID NO: 108, nucleotides 6-29 of SEQ ID NO: 109, nucleotides 6-30 of SEQ ID NO: 110, nucleotides 8-31 of SEQ ID NO: 111, nucleotides 6-29 of SEQ ID NO: 112, nucleotides 8-31 of SEQ ID NO: 113, nucleotides 5-29 of SEQ ID NO: 114, nucleotides 5-29 of SEQ ID NO: 115, nucleotides 4-28 of SEQ ID NO: 116, nucleotides 5-30 of SEQ ID NO: 117, nucleotides 8-28 of SEQ ID NO: 118, nucleotides 8-30 of SEQ ID NO: 119, nucleotides 8-29 of SEQ ID NO: 120, nucleotides 4-33 of SEQ ID NO: 121, nucleotides 7-34 of SEQ ID NO: 122, nucleotides 9-34 of SEQ ID NO: 123, nucleotides 8-34 of SEQ ID NO: 124, nucleotides 6-28 of SEQ ID NO: 125, nucleotides 7-28 of SEQ ID NO: 126, nucleotides 3-27 of SEQ ID NO: 127, nucleotides 7-32 of SEQ ID NO: 128, nucleotides 4-27 of SEQ ID NO: 129, and nucleotides 6-27 of SEQ ID NO: 130.

27. The method of claim 25, wherein detecting the presence or absence of the amplification product comprises hybridizing the amplified product with a molecular beacon comprising a polynucleotide sequence selected from the group consisting of SEQ ID NOs: 97-101 and 103-130.

* * * * *

SEQUENCE LISTING

```
<160> NUMBER OF SEQ ID NOS: 131

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgaaggaatg acggagta                                                   18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgccttagaa tattcatctc g                                               21

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcgacctgat cttatgttag cgcgattgga agagtccgta                           40

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 4
gaaccgatgg tgtggagccc acctgtgtcg gtt                               33

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctactaaccg ttctcatcgc                                              20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgttgatgg tgaccgtac                                               19

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaaactatag cgaaggaatg acgga                                        25

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taatttgccg agttccttaa cgaaag                                       26

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccccgaagat tccccttgat cgccgtagag cgatgagaac ggtt                   44

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtgtggagc gaggctttca agaaataata ttcatctcgc ccacctgtg    49

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgatcttatg ttagcggatt tgcctact    28

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttctagctg ttgatggtga ccgt    24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aactatagcg aaggaatgac ggag    24

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taatttgccg agttccttaa cgaaag    26

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccccgaagat tccccttgat cgccgtagag cgatgagaac ggtt    44

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtgtggagc gaggctttca agaaataata ttcatctcgc ccacctgtg         49

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgatcttatg ttagcggatt tgcctact         28

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttgatggtg accgtaccaa aacc         24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atagcgaagg aatgacggag taag         24

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
taatttgccg agttccttaa cgaaag         26

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccccgaagat tccccttgat cgccgtagag cgatgagaac ggtt         44

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtgtggagc gaggctttca agaaataata ttcatctcgc ccacctgtg    49

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gacctgatct tatgttagcg gatttgc    27

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttctagctg ttgatggtga ccgt    24

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agaagcgagt ccgggagat    19

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgctgaata ctacgctctc ctac    24

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccaacattcc aactgtcttc gaatcatcac tcagcccaga ccgccg    46

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcgtaacagc tcaccaatcg agaatcattg tcttatcgac acacccgc        48

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttacccactt agcataaaat tagggacctt aa        32

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgggactaa gcataaaacc gaca        24

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agaagcgagt ccgggagat        19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccggtacacc ttctctgctg        20

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aagccaacat tccaactgtc ttcgaatcat cagcccagac cgccg        45

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcgtaacagc tcaccaatcg agaatcattg tcttatcgac acacccgc        48

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttacccactt agcataaaat tagggacctt aa                                32

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgggactaa gcataaaacc gaca                                        24

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cacaggtggg cgagatgaat at                                          22

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctgacatatc cctttaacct tttggc                                      26

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atagtcaccc taaaaggctc cccttattcc aggcgcgcga gataacttt             49

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agaaatggcc caggcgactg tttaggcagg cgtcacacca tatact                46

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gggataattt gccgagttcc ttaacg                                          26

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
aaaacacagc actatgcaaa cctctaag                                        28

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
cacaggtggg cgagatgaat                                                 20

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ctgacatatc cctttaacct tttggc                                          26

<210> SEQ ID NO 45
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
atagtcaccc taaaaggctc cccttattcc aggcgcgcga gataacttt                 49

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
agaaatggcc caggcgactg tttaggcagg cgtcacacca tatact                    46

```
<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gggataattt gccgagttcc ttaacg                                        26

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aaaacacagc actatgcaaa cctctaag                                      28

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
attcgaagac agttggaatg t                                             21

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tattatcggc gcaatgattc tcgaggctta gaggcagcaa tc                      42

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtgagctgtt acgcactct                                                19

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tcgttactta tgccatggat c                                             21

<210> SEQ ID NO 53
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
taaacgggac taagcataaa accgaccttc tctgctgaat actacg            46

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gataagacac gcggtaggag                                         20

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cttaccaacg gaaatcaaac tc                                      22

<210> SEQ ID NO 56
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cacttagcat aaaattaggg accttaatcg gggggctaag cttcgt            46

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcggtctggg ctgttc                                             16

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tatcggcgca atgattctc                                          19

<210> SEQ ID NO 59
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgggtaagga agtgatgatt cgaagggtga gctgttacgc ac                        42

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tggcttagag gcagcaatc                                                  19

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atcggcgcaa tgattctcga tggcttagag gcagcaatc                            39

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgttacttat gccatggatc t                                               21

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
taagacacgc ggtaggaga                                                  19

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gaaatcgaag agattccctg tg                                              22

<210> SEQ ID NO 65
<211> LENGTH: 18
<212> TYPE: DNA
```

<213> ORGANISM: Artificial Sequence
<220> FEATURE:
<223> OTHER INFORMATION: Description of Artificial Sequence: Synthetic
     primer

<400> SEQUENCE: 65
ggtgttgagg tcggtctt                                                  18

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 66
ttatcctcaa tcctacaacc ccgagtagcg gcgagcgaaa g                         41

<210> SEQ ID NO 67
<211> LENGTH: 44
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 67
ggatcaggac tcctagttga acacactcct ttcgtctacg ggac                      44

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 68
ccttatcagc tcggtttagg c                                              21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 69
ggaaagatgg atgatacagg gtg                                            23

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 70
gttgtaggat tgaggataaa ggatc                                          25

<210> SEQ ID NO 71
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 71
tactggttca ctatcggtca tt                                                  22

<210> SEQ ID NO 72
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tcggtctttc tctcctttcg tctactccta gttgaacaca tctggaa                       47

<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cctcaacacc tgagtaggac tagacgcctt ggagagtggt ctc                           43

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggactatcac cctgtatcat cca                                                 23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgtgaaacct agtctgaatc tgg                                                 23

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76 tattccccctt tcgctcgc                                                      18

<210> SEQ ID NO 77
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 77
ggctattccc ctttcgctc                                                    19

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ttaggctatt cccctttcgc                                                   20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gctattcccc tttcgctcgc                                                   20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtttaggcta ttccccttc                                                    20

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgaaacatc ttagtaagca gagg                                              24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gtgtctagtc ctactcaggt g                                                 21

<210> SEQ ID NO 83
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
cctacaaccc cgagccttat caagagattc cctgtgtagc g                41

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggactcctag ttgaacacat ctggattctc tcctttcgtc tacgg            45

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gctcggttta ggctattccc                                        20

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aagatggatg atacagggtg atagt                                  25

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgaactgaaa catcttagta agcag                                  25

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctcctttcgt ctacgggact a                                      21

<210> SEQ ID NO 89
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
atcagctcgg tttaggctat tcccgaaaag aaatcgaaga gattccctg 49

<210> SEQ ID NO 90
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gctcggggtt gtaggattga ggatacctgt atcatccatc tttccagat 49

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ctttcgctcg ccgctac 17

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggatcaggac tcctagttga acac 24

<210> SEQ ID NO 93
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cctacaaccc cgagccttat cagaaaagaa atcgaagaga ttccctg 47

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
atcagctcgg tttaggctat tcccagagat tccctgtgta gcg 43

<210> SEQ ID NO 95
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 95
gctcggggtt gtaggattga ggatattctc tcctttcgtc tacgg            45

<210> SEQ ID NO 96
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gctcggggtt gtaggattga ggatactgta tcatccatct ttccagatgt       50

<210> SEQ ID NO 97
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
cgcgcacatc tggaaagatg gatgatacag ggtgcgcg                    38

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
cgtccaggac tcctagttga acacatctgg acg                         33

<210> SEQ ID NO 99
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ccggatcagg actcctagtt gaacacatct gatccgg                     37

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
cggccaggac tcctagttga acacatctgg ccg                         33

<210> SEQ ID NO 101
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
```

-continued cgtccggatc aggactccta gttgaacacc ggacg                                    35

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ctcgccacgt gaaacctagt ctgaatctgg cgag                                     34

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
ccgtggatga tacagggtga tagtccacgg                                          30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
cgtgggatga tacagggtga tagtcccacg                                          30

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
cggctcgaga ttccctgtgt agcggcgagc cg                                       32

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
cgccaggatc aggactccta gttgaacctg gcg                                      33

<210> SEQ ID NO 107
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107

```
caccgggatg atacagggtg atagtcccgg tc                                    32
```

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108

```
caccgggatg atacagggtg atagtcccgg tg                                    32
```

<210> SEQ ID NO 109
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109

```
tcgcgggatg atacagggtg atagtcccgc gg                                    32
```

<210> SEQ ID NO 110
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110

```
cagcgggatc aggactccta gttgaacccg ctg                                   33
```

<210> SEQ ID NO 111
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111

```
cacgctcgag attccctgtg tagcggcgag cgtg                                  34
```

<210> SEQ ID NO 112
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112

```
caggcggatc aggactccta gttgaacacc gcctg                                 35
```

<210> SEQ ID NO 113
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113

```
cagcgacaga aatcgaagag attccctgtg tcgctg                                36
```

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
cacgggatga tacagggtga tagtcccgtc                                        30

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
cacgggatga tacagggtga tagtcccgtg                                        30

<210> SEQ ID NO 116
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
cacgatggat gatacagggt gatagtccat cgtg                                   34

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
caccgatgga tgatacaggg tgatagtccc atcggtg                                37

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
cgcgatcgag gataaaggat caggactcga tcgcg                                  35

<210> SEQ ID NO 119
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
cgcgatcatt gaggataaag gatcaggact gatcgcg                                37

<210> SEQ ID NO 120
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
cgcgatcctc ctagttgaac acatctggag atcgcg                                  36

<210> SEQ ID NO 121
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
cgcgatcagg actcctagtt gaacacatct ggatcgcg                                38

<210> SEQ ID NO 122
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
cgcgactcag gactcctagt tgaacacatc tggagtcgcg                              40

<210> SEQ ID NO 123
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
cgcgatccgg ataaaggatc aggactccta gttgggatcg cg                           42

<210> SEQ ID NO 124
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
cgcgagtagg attgaggata aaggatcagg actcgcg                                 37

<210> SEQ ID NO 125
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
cgcgatccct gtgtagcggc gagcgagatc gcg                                     33

```
<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
cgcgatcctg tgtagcggcg agcgaaagat cgcg                                  34

<210> SEQ ID NO 127
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
cggctcgggg ttgtaggatt gaggatacga gccg                                  34

<210> SEQ ID NO 128
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
ccggagccta caaccccgag ccttatcagc tccgg                                 35

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
gcgcagctcg gtttaggcta ttcccctgcg cg                                    32

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
cgcggtctct cctttcgtct acgggaccgc g                                     31

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
cgcagtgaga gaaagaccga cctcaacact gcg                                   33
```